United States Patent [19]
Patton et al.

[11] Patent Number: 5,276,236
[45] Date of Patent: Jan. 4, 1994

[54] DISCRETE MOLECULAR SIEVE AND USE

[75] Inventors: Robert L. Patton, Katonah; Stephen T. Wilson, Shrub Oak, both of N.Y.; Gregory J. Gajda, Mt. Prospect, Ill.

[73] Assignee: UOP, Des Plaines, Ill.

[21] Appl. No.: 18,121

[22] Filed: Feb. 16, 1993

Related U.S. Application Data

[62] Division of Ser. No. 814,749, Dec. 26, 1991.

[51] Int. Cl.$^5$ ................................................ C07C 5/22
[52] U.S. Cl. .................................... 585/482; 585/480; 208/111; 208/120
[58] Field of Search ................ 585/480, 481, 482; 208/111, 120

[56] References Cited

U.S. PATENT DOCUMENTS

| | | | |
|---|---|---|---|
| 4,440,871 | 4/1984 | Lok et al. | 502/214 |
| 4,482,773 | 11/1984 | Chu et al. | 585/481 |
| 4,567,029 | 1/1986 | Wilson et al. | 423/306 |
| 4,740,650 | 5/1985 | Pellet et al. | 585/480 |
| 4,758,419 | 7/1988 | Lok et al. | 423/306 |
| 4,793,984 | 12/1988 | Lok et al. | 423/329 |
| 4,861,740 | 8/1989 | Sachtler et al. | 502/66 |
| 4,882,038 | 11/1989 | Lok et al. | 208/111 |

Primary Examiner—Carl F. Dees
Attorney, Agent, or Firm—Thomas K. McBride; John F. Spears, Jr.; Richard E. Conser

[57] ABSTRACT

This invention presents a novel MgAPSO molecular sieve, containing a critical range of magnesium in the sieve framework, which is particularly active for hydrocarbon conversion. The sieve advantageously is incorporated, along with a platinum-group metal, into a catalyst formulation which is useful for isomerization. When utilized in a process for isomerizing a non-equilibrium mixture of xylenes containing ethylbenzene, a greater yield of para-xylene is obtained compared to prior-art processes.

13 Claims, 4 Drawing Sheets

DISCRETE MOLECULAR SIEVE AND USE

CROSS REFERENCE TO RELATED APPLICATION

This application is a division of prior copending application Ser. No. 814,749, filed Dec. 26, 1991, the contents of which are incorporated herein by reference thereto.

FIELD OF THE INVENTION

This invention relates to an improved molecular sieve and its use for the conversion of hydrocarbons. More specifically, the invention concerns a magnesium-containing non-zeolitic molecular sieve which has a narrowly defined composition and is particularly useful for isomerization.

GENERAL BACKGROUND AND RELATED ART

A large variety of molecular sieves have been disclosed in the art as useful in catalysts for hydrocarbon conversion. The most well known are the crystalline aluminosilicate zeolites formed from corner-sharing $AlO_2$ and $SiO_2$ tetrahedra. The zeolites generally feature pore openings of uniform dimensions, significant ion-exchange capacity and the capability of reversibly desorbing an adsorbed phase which is dispersed throughout the internal voids of the crystal without displacing any atoms which make up the permanent crystal structure. Zeolites often are characterized by a critical, usually minimum, silica/alumina ratio.

More recently, a class of useful non-zeolitic molecular sieves containing framework tetrahedral units ($TO_2$) of aluminum ($AlO_2$), phosphorus ($PO_2$) and at least one additional element EL ($ELO_2$) has been disclosed. "Non-zeolitic molecular sieves" include the "ELAPSO" molecular sieves as disclosed in U.S. Pat. No. 4,793,984 (Lok et al.), "SAPO" molecular sieves of U.S. Pat. No. 4,440,871 (Lok et al.) and crystalline metal aluminophosphates—MeAPOs where "Me" is at least one of Mg, Mn, Co and Zn—as disclosed in U.S. Pat. No. 4,567,029 (Wilson et al.). Framework As, Be, B, Cr, Fe, Ga, Ge, Li, Ti or V and binary metal aluminophosphates are disclosed in various species patents. Particularly relevant to the present invention is U.S. Pat. No. 4,758,419 (Lok et al.), which discloses MgAPSO non-zeolitic molecular sieves. Generally the above patents teach a wide range of framework metal concentrations, e.g., the mole fraction of (magnesium+silicon) in Lok et al. '419 may be between 0.02 and 0.98 with a preferably upper limit of 0.35 mole fraction and magnesium concentration of at least 0.01.

The use of catalysts containing a zeolitic molecular sieve and magnesium for isomerization is disclosed in U.S. Pat. Nos. 4,482,773 (Chu et al.) and 4,861,740 (Sachtler et al.), but neither of these references disclose an isomerization catalyst containing non-zeolitic molecular sieves. The use of a catalyst containing a MgAPSO non-zeolitic molecular sieve in hydrocarbon conversion including isomerization is disclosed in the aforementioned U.S. Pat. No. 4,758,419 (Lok et al.). U.S. Pat. No. 4,740,650 (Pellet et al.) teaches xylene isomerization using a catalyst containing at least one non-zeolitic molecular sieve which may be MgAPSO. Neither Pellet et al. nor Lok et al., however, disclose or suggest the narrow criticality of the magnesium content of a non-zeolitic molecular sieve which is a feature of the present invention.

Catalysts for isomerization of $C_8$ aromatics ordinarily are classified by the manner of processing ethylbenzene associated with the xylene isomers. Ethylbenzene is not easily isomerized to xylenes, but it normally is converted in the isomerization unit because separation from the xylenes by superfractionation or adsorption is very expensive. A widely used approach is to dealkylate ethylbenzene to form principally benzene while isomerizing xylenes to a near-equilibrium mixture. An alternative approach is to react the ethylbenzene to form a xylene mixture in the presence of a solid acid catalyst with a hydrogenation-dehydrogenation function. The former approach commonly results in higher ethylbenzene conversion, thus lowering the quantity of recycle to the para-xylene recovery unit and concomitant processing costs, but the latter approach enhances xylene yield by forming xylenes from ethylbenzene. A catalytic composition and process which enhance conversion according to the latter approach, i.e., achieve ethylbenzene isomerization to xylenes with high conversion, would have significant utility.

SUMMARY OF THE INVENTION

A principal object of the present invention is to provide a novel molecular sieve which is useful for the conversion of hydrocarbons. More specifically, this invention is directed to a catalytic composition comprising a novel molecular sieve and a process for the isomerization of a mixture of xylenes and ethylbenzene resulting in improved yields and/or reduced processing costs.

This invention is based on the discovery that a MgAPSO molecular sieve having a framework magnesium content controlled within critical limits demonstrates a "volcano" effect in hydrocarbon-conversion activity.

Accordingly, a broad embodiment of the invention is directed toward a MgAPSO molecular sieve having a framework content of magnesium within a critical range. Preferably the sieve is incorporated into a catalytic composition comprising a platinum-group metal; the optimal catalytic composition also contains an inorganic-oxide matrix. In an alternative embodiment, the catalytic composition also comprises an $AlPO_4$ molecular sieve.

Another embodiment is directed toward a process for hydrocarbon conversion using a catalytic composition containing a MgAPSO molecular sieve having a content of magnesium within a critical range. Preferably the process comprises isomerization, more preferably of a feed stream comprising a non-equilibrium mixture of xylenes and ethylbenzene at isomerization conditions to obtain a product having an increased para-xylene content.

These as well as other objects and embodiments will become evident from the following detailed description of the invention.

DETAILED DESCRIPTION OF THE INVENTION

Figure 1:
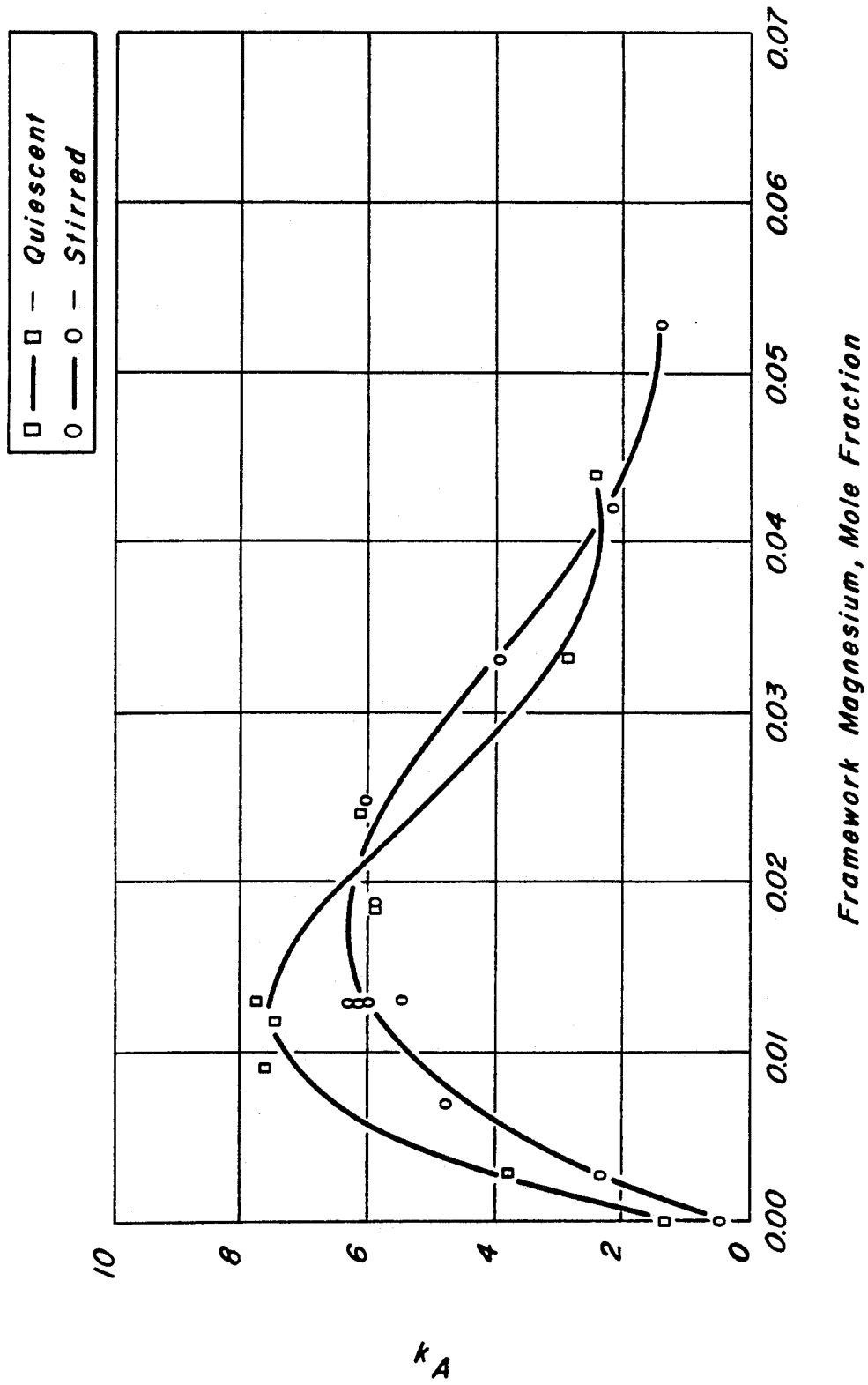
FIG. 1 compares the activity $k_A$ of MgAPSO molecular sieves having a range of framework magnesium contents.

As mentioned above, this invention is drawn to a MgAPSO molecular sieve having a framework content of magnesium within a critical range.

The MgAPSO molecular sieve of the invention can be understood by reference to the disclosure of U.S. Pat. No. 4,758,419, incorporated herein by reference thereto. MgAPSO sieves have a microporous crystalline framework structure of $MgO_2^{-2}$, $AlO_2^{-}$, $PO_2^{+}$, and $SiO_2$ tetrahedral units having an empirical chemical composition on an anhydrous basis expressed by the formula:

$$mR:(Mg_wAl_xP_ySi_z)O_2$$

wherein "R" represents at least one organic templating agent present in the intracrystalline pore system; "m" represents the molar amount of "R" present per mole of $(Mg_wAl_xP_ySi_z)O_2$ and has a value of zero to about 0.3; and "w", "x", "y" and "z" represent the mole fractions of element magnesium, aluminum, phosphorus and silicon, respectively, present as tetrahedral oxides. The mole fraction of each framework constituent of the molecular sieve is defined as a compositional value which is plotted in phase diagrams of U.S. Pat. No. 4,758,419. The mole fractions "w", "x", "y" and "z" are generally defined as being within the limiting compositional values or points as follows:

| Point | Mole Fraction | | |
|-------|------|------|---------|
|       | x    | y    | (z + w) |
| A     | 0.60 | 0.38 | 0.02    |
| B     | 0.39 | 0.59 | 0.02    |
| C     | 0.01 | 0.60 | 0.39    |
| D     | 0.01 | 0.01 | 0.98    |
| E     | 0.60 | 0.01 | 0.39    |

It is an essential aspect of the present invention that the magnesium content of the MgAPSO sieve is controlled within narrow limits. Specifically, the mol fraction "w" of framework magnesium in the molecular sieves of the invention is between about 0.003 and 0.035. Best results are obtained when the mol fraction of framework magnesium is between about 0.005 and 0.025.

A "volcano" effect has been observed on butane-cracking activity "$k_A$" when the magnesium content of the sieves is controlled within the above limits according to the invention. Volcano effect refers to an unusual and surprising increase in $k_A$ for sieves of the invention relative to sieves having both higher and lower magnesium contents. Butane-cracking activity is a readily determined representation of hydrocarbon-conversion activity in such processing areas as isomerization, reforming, dehydrocyclization, dehydrogenation, disproportionation, transalkylation, dealkylation, alkylation, polymerization, and catalytic cracking.

The butane cracking activity $k_A$ is determined by testing an 0.5 to 5-gram sample of 20-40 mesh MgAPSO sieve particles loaded into a cylindrical quartz tube, as described more specifically hereinafter in Example II. The quantity of sieves is selected to effect butane conversion of from 5% to 90% when butane is present in a concentration of 2 mole % in a helium carrier. The feedstock and reactor effluent are analyzed by conventional gas chromatography, and the pseudo-first-order rate constant $k_A$ is calculated from the analytical data.

The nomenclature employed herein to refer to the members of the class of MgAPSOs is consistent with that employed in the aforementioned patents. A particular member of a class is generally referred to as a "—n" species wherein "n" is an integer, e.g., MgAPSO-11, MgAPSO-31 and MgAPSO-41. The especially preferred species of the present invention is MgAPSO-31 having a characteristic X-ray powder diffraction pattern which contains at least the d-spacings set forth below:

| 2θ          | d           | Relative Intensity |
|-------------|-------------|--------------------|
| 8.4–9.501   | 10.53–9.3084 | w-s               |
| 20.2–20.4   | 4.40–4.35   | m                  |
| 22.0–22.1   | 4.04–4.022  | m                  |
| 22.5–22.7   | 3.952–3.92  | vs                 |
| 23.15–23.35 | 2.831–2.814 | w-m                |

MgAPSO sieves generally are synthesized by hydrothermal crystallization from an aqueous reaction mixture containing reactive sources of magnesium, silicon, aluminum and phosphorus and an organic templating agent for an effective time at effective conditions of pressure and temperature. The reaction-mixture compositions preferably are expressed in terms of molar ratios as follows:

$$aR:(Mg_rAl_sP_tSi_u)bH_2O$$

wherein (r+s+t+u)=1.00 mole such that the aforementioned framework constituents "w", "x", "y" and "z" of the molecular sieves have the compositional values as described, the amount of organic templating agent "a" has a preferably positive value between 0 and about 6, and the amount of water "b" is between 0 and 500 with a preferable value between 2 and 300.

The organic templating agent, if any, can be selected from among those disclosed in U.S. Pat. No. 4,758,419. Generally this agent will contain one or more elements selected from Group VA (IUPAC 15) of the Periodic Table [See Cotton and Wilkinson, *Advanced Inorganic Chemistry*, John Wiley & Sons (Fifth Edition, 1988)], preferably nitrogen or phosphorus and especially nitrogen, and at least one alkyl or aryl group having from 1 to 8 carbon atoms. Preferred compounds include the amines and the quaternary phosphonium and quaternary ammonium compounds. Mono-, di- and tri-amines are advantageously utilized, either alone or in combination with a quaternary ammonium compound. Especially preferred amines include di-isopropylamine, di-n-propylamine, triethylamine and ethylbutylamine.

The reaction source of silicon may be silica, either as a silica sol or as fumed silica, a reactive solid amorphous precipitated silica, silica gel, alkoxides of silicon, silicic acid or alkali metal silicate and mixtures thereof.

The most suitable reactive source of phosphorus yet found for the instant process is phosphoric acid, but organic phosphates such as triethyl phosphate have been found satisfactory, and so also have crystalline or amorphous aluminophosphates such as the AlPO$_4$ composition of U.S. Pat. No. 4,310,440. Organo-phosphorus compounds selected as templating agents do not, apparently, serve as reactive sources of phosphorus, but these compounds may be transformed in situ to a reactive source of phosphorus under suitable process conditions.

The preferred aluminum source is either an aluminum alkoxide, such as aluminum isoproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The reactive source of magnesium can be introduced into the reaction system in any form which permits the formation in situ of a reactive form of magnesium, i.e., reactive to form the framework tetrahedral unit $MgO_2^{-2}$. Compouunds of magnesium which may be employed include oxides, hydroxides, alkoxides, nitrates, sulfates, halides, carboxylates (e.g. acetates and the like), organo-metallics and mixtures thereof.

Crystallization generally is effected in a sealed pressure vessel, preferably lined with an inert plastic material such as polytetrafluoroethylene. While not essential to the synthesis of MgAPSO compositions, stirring or other moderate agitation of the reaction mixture and/or seeding the reaction mixture with seed crystals of either the MgAPSO species to be produced or a topologically similar aluminophosphate, aluminosilicate or other molecular sieve composition facilitates the crystallization procedure. The reaction mixture is maintained advantageously under autogenous pressure at a temperature between 50° and 250°, and preferably between 100° and 200° C., for a period of several hours to several weeks. The crystallization period advantageously will be between about 4 hours and 20 days. The MgAPSO product is recovered by any convenient method such as centrifugation or filtration.

After crystallization the MgAPSO product may be isolated and advantageously washed with water and dried in air. The as-synthesized MgAPSO will typically contain within its internal pore system at least one form of any templating agent, also referred to herein as the "organic moiety", employed in its formation. Most commonly the organic moiety is present, at least in part, as a charge-balancing cation. In some cases, the MgAPSO pores are sufficiently large and the organic molecule sufficiently small that the removal of the latter may be effected by conventional desorption procedures. Generally, however, the organic moiety is an occluded molecular species which is too large to move freely through the pore system of the MgAPSO product and must be thermally degraded and removed by calcining at temperatures of from 200° to 700° C.

The MgAPSO compositions are formed from $MgO_2$, $AlO_2$, $PO_2$ and $SiO_2$ tetrahedral units which, respectively, have a net charge of $-2$, $-1$, $+1$ and 0. An $AlO_2^-$ tetrahedron can be balanced electrically either by association with a $PO_2^+$ tetrahedron or a simple cation such as an alkali metal cation, a proton (H$^+$), a cation of magnesium present in the reaction mixture, or an organic cation derived from the templating agent. Similarly, an $MgO_2^{-2}$ tetrahedron can be balanced electrically by association with $PO_2^+$ tetrahedra, a simple cation such as alkali metal cation, a proton (H$^+$), a cation of the magnesium, organic cations derived from the templating agent, or other divalent or polyvalent metal cations introduced from an extraneous source. Ion exchange of MgAPSO compositions will ordinarily be possible only after the organic moiety present as a result of synthesis has been removed from the pore system.

It is within the scope of the invention that a catalytic composition prepared from the MgAPSO of the invention comprises one or more additional non-zeolitic molecular sieves. Preferably the non-zeolitic molecular sieves are as a multi-compositional, multi-phase composite having contiguous phases, a common crystalline framework structure and exhibiting a distinct heterogeneity in composition, especially wherein one phase comprises a deposition substrate upon which another phase is deposited as an outer layer. Such composites are described in U.S. Pat. No. 4,861,739, incorporated herein by reference thereto. Suitable non-zeolitic molecular sieves include but are not limited to those of U.S. Pat. Nos. 4,440,871, 4,567,029 and 4,793,984, incorporated by reference. In a highly preferred embodiment the layered catalytic composition comprises a crystalline aluminophosphate of U.S. Pat. Nos. 4,310,440, incorporated by reference. The AlPO$_4$ of this embodiment is a crystalline metallophosphate whose essential framework structure has a chemical composition, expressed in terms of molar ratios of oxides, of:

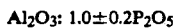

$Al_2O_3$: $1.0 \pm 0.2 P_2O_5$

AlPO$_4$-31 is especially preferred as a substrate and a MgAPSO, especially MgAPSO-31, as an outer layer.

A catalytic composition preferably is prepared by combining the molecular sieves of the invention with a binder for convenient formation of catalyst particles. The binder should be porous, adsorptive support having a surface area of about 25 to about 500 m$^2$/g, uniform in composition and relatively refractory to the conditions utilized in the hydrocarbon conversion process. The term "uniform in composition" denotes a support which is unlayered, has no concentration gradients of the species inherent to its composition, and is completely homogeneous in composition. Thus, if the support is a mixture of two or more refractory materials, the relative amounts of these materials will be constant and uniform throughout the entire support., It is intended to include within the scope of the present invention carrier materials which have traditionally been utilized in hydrocarbon conversion catalysts such as: (1) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, etc.; (2) ceramics, porcelain, bauxite; (3) silica or silica gel, silicon carbide, clays and silicates including those synthetically prepared and naturally occurring, which may or may not be acid treated, for example attapulgus clay, diatomaceous earth, fuller's earth, kaolin, kieselguhr, etc.; (4) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations, (5) spinels such as $MgAl_2O_4$, $FeAl_2O_4$, $ZnAl_2O_4$, $CaAl_2O_4$, and other like compounds having the formula $MO-Al_2O_3$ where M is a metal having a valence of 2; and (6) combinations of materials from one or more of these groups.

The preferred matrices for use in the present invention are refractory inorganic oxides, with best results obtained with a binder comprised of alumina. Suitable aluminas are the crystalline aluminas known as the gamma-, eta-, and theta-aluminas. Excellent results are obtained with a matrix of substantially pure gamma-alumina. In addition, in some embodiments, the alumina matrix may contain minor proportions of other well known refractory inorganic oxides such as silica, zirconia, magnesia, etc. Whichever type of matrix is employed, it may be activated prior to use by one or more treatments including but not limited to drying, calcination, and steaming.

Using techniques commonly known to those skilled in the art, the catalytic composition of the instant invention may be composited and shaped into any useful form such as spheres, pills, cakes, extrudates, powders, granules, tablets, etc., and utilized in any desired size. These shapes may be prepared utilizing any known forming operations including spray drying, tabletting, spherizing, extrusion, and nodulizing.

A preferred shape for the catalyst composite is an extrudate. The well-known extrusion method initially involves mixing of the non-zeolitic molecular sieve, either before or after adding metallic components, with the binder and a suitable peptizing agent to form a homogeneous dough or thick paste having the correct moisture content to allow for the formation of extrudates with acceptable integrity to withstand direct calcination. Extrudability is determined from an analysis of the moisture content of the dough, with a moisture content in the range of from 30 to 50 wt. % being preferred. The dough then is extruded through a die pierced with multiple holes and the spaghetti-shaped extrudate is cut to form particles in accordance with techniques well known in the art. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

An alternative shape of the composite is a sphere, continuously manufactured by the well-known oil drop method. Preferably, this method involves dropping the mixture of molecular sieve, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50°–200° C. and subjected to a calcination procedure at a temperature of about 450°–700° C. for a period of about 1 to about 20 hours. This treatment effects conversion of the hydrogel to the corresponding alumina matrix.

A preferred component of the present catalytic composition is a platinum-group metal including one or more of platinum, palladium, rhodium, ruthenium, osmium, and iridium. The preferred platinum-group metal is platinum. The platinum-group metal component may exist within the final catalyst composite as a compound such as an oxide, sulfide, halide, oxysulfide, etc., or as an elemental metal or in combination with one or more other ingredients of the catalytic composition. It is believed that the best results are obtained when substantially all the platinum-group metal component exists in a reduced state. The platinum-group metal component generally comprises from about 0.01 to about 2 mass % of the final catalytic composite, calculated on an elemental basis.

The platinum-group metal component may be incorporated into the catalyst composite in any suitable manner. The preferred method of preparing the catalyst normally involves the utilization of a water-soluble, decomposable compound of a platinum-group metal to impregnate the calcined zeolite/binder composite. For example, the platinum-group metal component may be added to the calcined hydrogel by commingling the calcined composite with an aqueous solution of chloroplatinic or chloropalladic acid.

It is within the scope of the present invention that the catalytic composition may contain other metal components known to modify the effect of the platinum-group metal component. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalyst by any means known in the art.

The catalytic composition of the present invention may contain a halogen component. The halogen component may be either fluorine, chlorine, bromine or iodine or mixtures thereof. Chlorine is the preferred halogen component. The halogen component is generally present in a combined state with the inorganic-oxide support. The halogen component is preferably well dispersed throughout the catalyst and may comprise from more than 0.2 to about 15 wt %, calculated on an elemental basis, of the final catalyst.

The halogen component may be incorporated in the catalytic composition in any suitable manner, either during the preparation of the inorganic-oxide support or before, while or after other catalytic components are incorporated. For example, the carrier material may contain halogen and thus contribute at least some portion of the halogen content in the final catalyst. The halogen component or a portion thereof also may be added to the catalyst during the incorporation of other catalyst components into the support, for example, by using chloroplatinic acid in impregnating a platinum component. Also, the halogen component or a portion thereof may be added to the catalyst by contacting with the halogen or a compound, solution, suspension or dispersion containing the halogen before or after other catalyst components are incorporated into the support.

The catalyst composite is dried at a temperature of from about 100° to about 320° C. for a period of from about 2 to about 24 or more hours and calcined at a temperature of from 400° to about 650° C. in an air atmosphere for a period of from about 0.1 to about 10 hours until the metallic compounds present are converted substantially to the oxide form. The optional halogen component may be adjusted by including a halogen or halogen-containing compound in the air atmosphere.

The resultant calcined composite may be subjected to a substantially water-free reduction step to insure a uniform and finely divided dispersion of the optional metallic components. Preferably, substantially pure and dry hydrogen (i.e., less than 20 vol. ppm $H_2O$) is used as the reducing agent in this step. The reducing agent contacts the catalyst at conditions, including a temperature of from about 200° to about 650° C. and for a period of from about 0.5 to about 10 hours, effective to reduce substantially all of the Group VIII metal component to the metallic state.

The resulting reduced catalytic composite may, in some cases, be beneficially subjected to a presulfiding operation designed to incorporate in the catalytic composite from about 0.05 to about 0.5 mass % sulfur calculated on an elemental basis. Preferably, this presulfiding treatment takes place in the presence of hydrogen and a suitable sulfur-containing compound such as hydrogen sulfide, lower molecular weight mercaptans, organic sulfides. etc. Typically, this procedure comprises treating the reduced catalyst with a sulfiding gas such as a mixture of hydrogen and hydrogen sulfide having about 10 moles of hydrogen per mole of hydrogen sulfide at conditions sufficient to effect the desired incorporation of sulfur, generally including a temperature ranging from about 10° up to about 593° C. or more. It is generally a good practice to perform this presulfiding step operation under substantially water-free conditions.

MgAPSO sieves of the invention are useful for the conversion of hydrocarbons to obtain a converted product. The sieves preferably are utilized in combination with at least one inorganic-oxide matrix and one or more metals as described herein. A hydrocarbon feedstock is converted at hydrocarbon-conversion conditions including a pressure of about atmospheric to 200 atmospheres, temperatures of about 50° to 600° C., liquid hourly space velocities of from about 0.1 to 100 $hr^{-1}$, and if hydrogen is present, hydrogen-to-hydrocarbon molar ratios of from about 0.1 to 80.

Hydrocarbon-conversion processes which would advantageously employ catalytic compositions containing the MgAPSO sieves of the invention include isomerization, reforming, dehydrocyclization, dehydrogenation, disproportionation, transalkylation, dealkylation, alkylation, polymerization, hydrocracking and catalytic cracking.

MgAPSO catalyst compositions used in reforming processes preferably contain a hydrogenation promoter such as a platinum-group metal, optionally one or more modifiers such as rhenium and Group IVA (14) metals, and an inorganic-oxide binder. Hydrocarbon feedstocks, preferably naptha, contact the catalyst at pressures of between atmospheric and 40 atmospheres, temperatures of about 350° to 600° C., liquid hourly space velocities (LHSV) from 0.2 to 20 $hr^{-1}$, and hydrogen-to-hydrocarbon molar ratios of from about 0.1 to 10. Dehydrocyclization of naphthas and other paraffin-containing stocks is carried out over a similar catalyst, preferably nonacidic through incorporation of an alkali or alkaline earth metal, at similar conditions with operating pressure no higher than about 15 atmospheres. Products of reforming and dehydrocyclization generally have an increased concentration of aromatics relative to the feedstocks.

Isomerization of light hydrocarbons is advantageously effected using MgAPSO catalyst compositions within the scope of those described for use in reforming processes. The light hydrocarbon feedstock contacts the catalyst at pressures of between atmospheric and 70 atmospheres, temperatures of about 50° to 300°, LHSV from 0.2 to 5 $hr^{-1}$, and hydrogen-to-hydrocarbon molar ratios of from about 0.1 to 5. Isomerization of olefins such as butenes, pentenes and higher olefins is effected over a catalyst which preferably does not contain a substantial hydrogenation component, in order to avoid olefin hydrogenation, at somewhat higher temperatures of 200° to 600° C. and higher space velocities of 0.5 to 100 $hr^{-1}$. Usually isomerization yields a product having a greater concentration of branched hydrocarbons.

Heavier paraffins, waxy distillates and raffinates are isomerized to increase the branching of the hydrocarbons using essentially the same catalyst compositions as used in reforming. Operating conditions include pressures of between about 20 and 150 atmospheres, temperatures of about 200° to 450° C., LHSV from 0.2 to 10 $hr^{-1}$, and hydrogen-to-hydrocarbon molar ratios of from about 0.5 to 10.

MgAPSO catalyst compositions used in hydrocracking processes preferably contain a hydrogenation promoter such as one or more of Group VIII (8–10) and Group VIB (6) metals and an inorganic-oxide matrix. A variety of feedstocks including atmospheric and vacuum distillates, cycle stocks and residues are cracked to yield lighter products at pressures of between 30 and 200 atmospheres, temperatures of about 200° to 450° C., LHSV from 0.1 to 10 $hr^{-1}$, and hydrogen-to-hydrocarbon molar ratios of from about 2 to 80.

Catalyst compositions of the same general description as those used in hydrocracking processes are useful in hydrotreating and hydrofining. A variety of naphthas, atmospheric and vacuum distillates, cracked and cycle stocks and residues are treated to remove sulfur, nitrogen and other heteroatoms and to saturate unsaturates at pressures of between 30 and 150 atmospheres, temperatures of about 200° to 450° C., LHSV from 0.1 to 20 $hr^{-1}$, and hydrogen-to-hydrocarbon molar ratios of from about 2 to 20. Operating conditions vary with respect to the difficulty of heteroatom removal, usually relating to the size and aromaticity of the containing molecules, and the concentration particularly of nitrogen in the feedstock. Products meet environmental requirements, are not as corrosive or contaminating of downstream equipment, or effect less deactivation of catalysts in downstream-processing units relative to the feedstock.

Disproportionation also is effected with MgAPSO catalyst compositions as described above in relation to reforming processes; optionally, the catalyst also contains one or more Group VIA (6) metals. Suitable feedstocks include single-ring aromatics, naphthalenes and light olefins, and the reaction yields more valuable products of the same hydrocarbon specie. Isomerization and transalkylation also may occur at the operating conditions of between 10 and 70 atmospheres, temperatures of about 200° to 500° C., and LHSV from 0.1 to 10 $hr^{-1}$. Hydrogen is optionally present at a molar ratio to hydrocarbon of from about 0.1 to 10.

A particularly advantageous use for the MgAPSO sieves of the invention is in the isomerization of isomerizable alkylaromatic hydrocarbons of the general formula $C_6H_{(6-n)}R_n$, where n is an integer from 2 to 5 and R is $CH_3$, $C_2H_5$, $C_3H_7$, or $C_4H_9$, in any combination and including all the isomers thereof to obtain more valuable isomers of the alkylaromatic. Suitable alkylaromatic hydrocarbons include, for example, ortho-xylene, meta-xylene, para-xylene, ethylbenzene, ethyltoluenes, trimethylbenzenes, diethylbenzenes, triethyl-benzenes, methylpropylbenzenes, ethylpropylbenzenes, diisopropylbenzenes, and mixtures thereof.

Isomerization of a $C_8$-aromatic mixture containing ethylbenzene and xylenes is a particularly preferred application of the MgAPSO sieves of the invention.

Generally such mixture will have an ethylbenzene content in the approximate range of 5 to 50 mass %, an ortho-xylene content in the approximate range of 0 to 35 mass %, a meta-xylene content in the approximate range of 20 to 95 mass % and a para-xylene content in the approximate range of 0 to 15 mass %. It is preferred that the aforementioned $C_8$ aromatics comprise a non-equilibrium mixture, i.e., at least one $C_8$-aromatic isomer is present in a concentration that differs substantially from the equilibrium concentration at isomerization conditions. Usually the non-equilibrium mixture is prepared by removal of para-and/or ortho-xylene from a fresh $C_8$ aromatic mixture obtained from an aromatics-production process.

The alkylaromatic hydrocarbons may be utilized in the present invention as found in appropriate fractions from various refinery petroleum streams, e.g., as individual components or as certain boiling-range fractions obtained by the selective fractionation and distillation of catalytically cracked or reformed hydrocarbons. The isomerizable aromatic hydrocarbons need not be concentrated, but may be present in minor quantities in various streams. The process of this invention allows the isomerization of alkylaromatic-containing streams such as catalytic reformate with or without subsequent aromatics extraction to produce specified xylene isomers, particularly para-xylene. A $C_8$-aromatics feed to the present process may contain nonaromatic hydrocarbons i.e., naphthenes and paraffins, in an amount up to 30 mass %.

According to the process of the present invention, an alkylaromatic hydrocarbon charge stock, preferably in admixture with hydrogen, is contacted with a catalyst of the type hereinabove described in an alkylaromatic hydrocarbon isomerization zone. Contacting may be effected using the catalyst in a fixed-bed system, a moving-bed system, a fluidized-bed system, or in a batch-type operation. In view of the danger of attrition loss of the valuable catalyst and of the simpler operation, it is preferred to use a fixed-bed system. In this system, a hydrogen-rich gas and the charge stock are preheated by suitable heating means to the desired reaction temperature and then passed into an isomerization zone containing a fixed bed of catalyst. The conversion zone may be one or more separate reactors with suitable means therebetween to ensure that the desired isomerization temperature is maintained at the entrance to each zone. The reactants may be contacted with the catalyst bed in either upward-, downward-, or radial-flow fashion, and the reactants may be in the liquid phase, a mixed liquid-vapor phase, or a vapor phase when contacted with the catalyst.

The alkylaromatic charge stock, preferably a non-equilibrium mixture of $C_8$ aromatics, is contacted with a catalytic combination as hereinbefore described in an isomerization zone while maintaining the zone at appropriate alkylaromatic-isomerization conditions. The conditions comprise a temperature ranging from about 0° to 600° C. or more, and preferably is in the range of from about 300° to 500° C. The pressure generally is from about 1 to 100 atmospheres absolute, preferably less than about 50 atmospheres. Sufficient catalyst is contained in the isomerization zone to provide a liquid hourly space velocity of charge stock of from about 0.1 to 30 $hr^{-1}$, and preferably 0.5 to 10 $hr^{-1}$. The hydrocarbon charge stock optimally is reacted in admixture with hydrogen at a hydrogen/hydrocarbon mole ratio of about 0.5:1 to about 25:1 or more. Other inert diluents such as nitrogen, argon and light hydrocarbons may be present.

The particular scheme employed to recover an isomerized product from the effluent of the reactors of the isomerization zone is not deemed to be critical to the instant invention, and any effective recovery scheme known in the art may be used. Typically, the reactor effluent will be condensed and the hydrogen and light-hydrocarbon components removed therefrom by flash separation. The condensed liquid product then is fractionated to remove light and/or heavy byproducts and obtain the isomerized product. In some instances, certain product species such as ortho-xylene may be recovered from the isomerized product by selective fractionation. The product from isomerization of $C_8$ aromatics usually is processed to selectively recover the para-xylene isomer, optionally by crystallization. Selective adsorption is preferred using crystalline aluminosilicates according to U.S. Pat. No. 3,201,491. Improvements and alternatives within the preferred adsorption recovery process are described in U.S. Pat. Nos. 3,626,020, 3,696,107, 4,039,599, 4,184,943, 4,381,419 and 4,402,832, incorporated herein by reference thereto.

In a separation/isomerization process combination relating to the processing of an ethylbenzene/xylene mixture, a fresh $C_8$-aromatic feed is combined with isomerized product comprising $C_8$ aromatics and naphthenes from the isomerization reaction zone and fed to a para-xylene separation zone; the para-xylene-depleted stream comprising a non-equilibrium mixture of $C_8$ aromatics is fed to the isomerization reaction zone, where the $C_8$-aromatic isomers are isomerized to near-equilibrium levels to obtain the isomerized product. In this process scheme non-recovered $C_8$-aromatic isomers preferably are recycled to extinction until they are either converted to para-xylene or lost due to side-reactions. Ortho-xylene separation, preferably by fractionation, also may be effected on the fresh $C_8$-aromatic feed or isomerized product, or both in combination, prior to para-xylene separation.

The following examples are presented for purpose of illustration only and are not intended to limit the scope of the present invention.

EXAMPLES

The following examples are presented for purpose of illustration only and are not intended to limit the scope of the present invention. The examples demonstrate the criticality of magnesium content in molecular sieves of the invention by butane-cracking activity, relate butane-cracking and isomerization activity, and demonstrate the utility of the catalyst for isomerization of $C_8$ aromatics.

MgAPSO-31 compositions have been prepared and tested employing reaction mixtures having a molar composition expressed as:

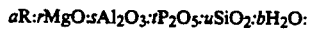

$aR:rMgO:sAl_2O_3:tP_2O_5:uSiO_2:bH_2O$:

wherein the values a, r, s, t, u and b represent moles of template R, magnesium (expressed as the oxide), $Al_2O_3$, $P_2O_5$ ($H_3PO_4$ expressed as $P_2O_5$), $SiO_2$ and $H_2O$, respectively. The values ranged as follows, based on t=1:

| | |
|---|---|
| a | 1.5–2.0 |
| r | as described hereinbelow |
| s | 0.75–1.1 |
| u | 0.1–1.2 (usually 0.6) |

| -continued | |
|---|---|
| b | 40-80 |

These ranges do not, however, limit the applicability of the present invention as described hereinabove.

EXAMPLE I

Tests are reported below for MgAPSO-31 compositions prepared via reaction mixtures having a molar composition of about:

$1.5R : rMgO : 0.9Al_2O_3 : P_2O_5 : 0.3SiO_2 : 50H_2O$:

The value r was varied to provide a range of mol fractions of framework magnesium in the context of the previously defined formula:

$(Mg_wAl_xP_ySi_z)$ wherein $(w+x+y+z) = 1.00$ and w is the mol fraction of framework magnesium.

The reaction mixture was prepared by mixing the Al₂O₃ as pseudoboehmite (Versal 250) into the H₃PO₄ and water on a gradual basis and blending until a homogeneous mixture was observed. Magnesium acetate was dissolved in a portion of the water and then was added followed by addition of LUDOX-LS. The combined mixture was blended until a homogeneous mixture was observed. The organic templating agent (ethylbutylamine) and AlPO₄-31 seed were added to this mixture and blended until a homogeneous mixture was observed. Portions of the resulting mixture were placed in either lined (polytetrafluoroethylene) stainless steel pressure vessels for quiescent crystallization or an unlined stirred stainless steel pressure vessel and heated up to about 200° C. to effect crystallization at autogenous pressure. The products were removed from the reaction vessel, cooled and evaluated as set forth hereinafter.

The examples present test results obtained when catalysts of the invention were evaluated in an isomerization process. The catalysts were evaluated using a pilot plant flow reactor processing a non-equilibrium C₈ aromatic feed comprising 52.0 mass % meta-xylene, 18.5 mass % ortho-xylene, 0.1 mass % para-xylene, 21.3 mass % ethylbenzene, and 0.1 mass % toluene, with the balance being nonaromatic hydrocarbons. This feed was contacted with 100 cc of catalyst at a liquid hourly space velocity of 2, and a hydrogen/hydrocarbon mole ratio of 4. Reactor pressure and temperature were adjusted to cover a range of conversion values in order to develop the relationship between C₈ ring loss and approach to xylene equilibrium (as determined by product para-xylene to total xylene mole ratio). At the same time, at each temperature, the pressure was chosen to maintain a constant mole ratio of C₈ naphthenes to C₈ aromatics of approximately 0.06.

EXAMPLE II

A representation of the hydrocarbon-conversion activity of the present class of medium-pore molecular sieves is the butane-cracking activity "$k_A$" determined using a bench-scale apparatus. This activity measurement allows larger number of samples to be surveyed with more consistent results than, e.g., isomerization performance in a pilot plant. The reactor is a cylindrical quartz tube having a length of 254 mm and an I.D. of 10.3 mm. In each test the reactor was loaded with 20–40 mesh (U.S. std.) particles of the MgAPSO-31 molecular sieve in an amount of from 0.5 to 5 grams, the quantity being selected so that the conversion of n-butane was at least 5% and not more than 90% under the test conditions. As-synthesized samples containing organics are first calcined in situ in the reactor in air at 600° C. for one hour to remove organic materials from the pore system, then in a flowing stream of helium at 500° C. for at least 10 minutes. The activity $k_A$ then was determined using a feedstock consisting of a helium/n-butane mixture containing 2 mole percent n-butane which is passed through the reactor at a rate of 50 cc/minute. The feedstock and the reactor effluent were analyzed using conventional gas chromatography techniques, reactor effluent being analyzed after 10 minutes of on-stream operation at 500° C. The pseudo-first-order rate constant $k_A$ was calculated from the analytical data.

Eighteen samples of MgAPSO-31 with varying magnesium contents, and two controls without magnesium, were prepared according to the procedure of Example I. Crystallization was carried out at 200° C. with eight samples in a quiescent reaction mixture and ten stirred samples. The activity $k_A$ of the samples was determined according to the procedure described hereinabove and plotted in FIG. 1. The samples showed particularly high activities in the region of 0.005–0.025 mole fraction of magnesium, with some increased activity at 0.003 and 0.03–0.035 mole fraction magnesium and low activities at the outer limits of the tests. Activities of the eleven most active samples in the middle of the range were twice or three times those of samples containing the highest concentrations of framework magnesium.

EXAMPLE III

Figure 2:
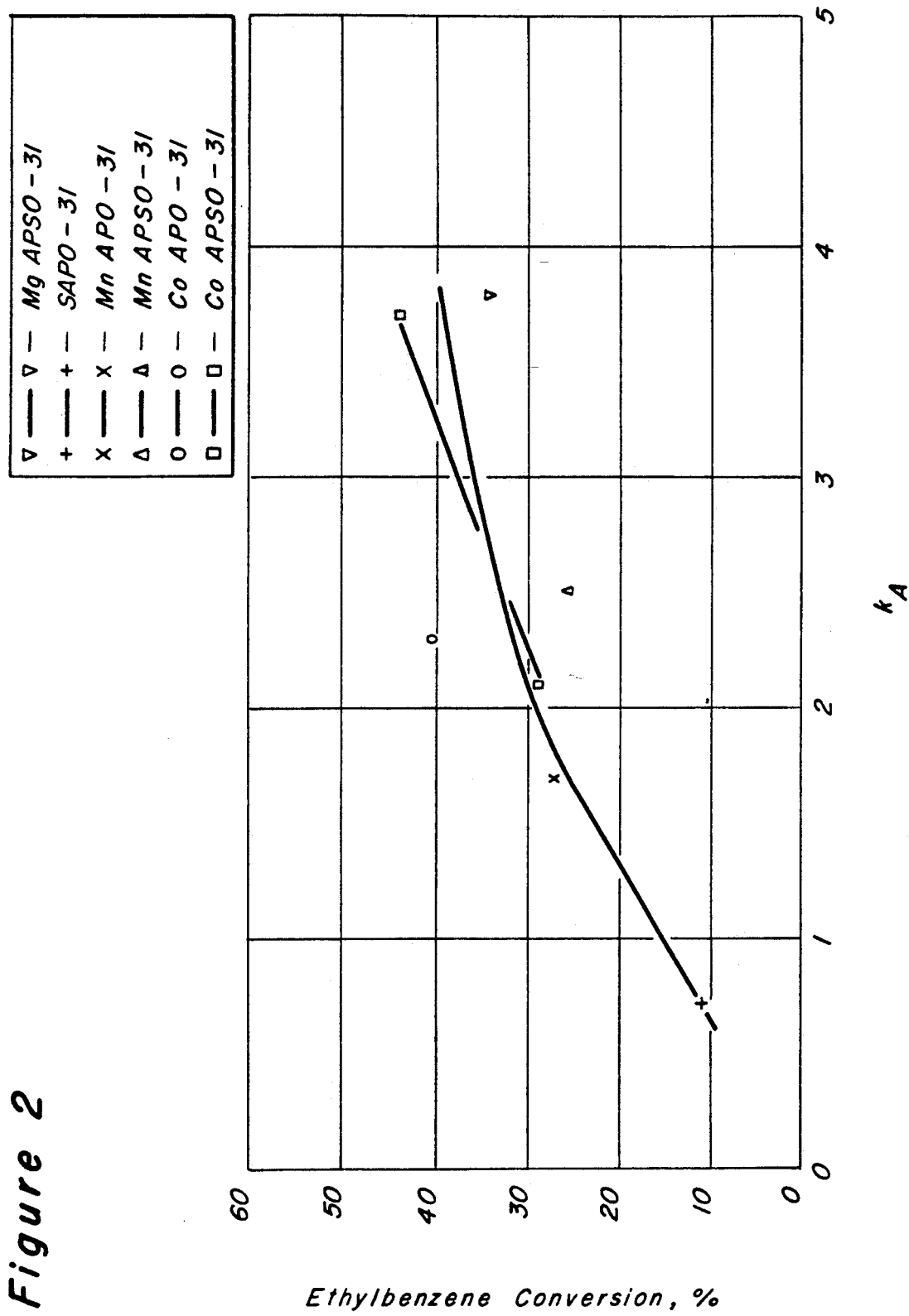
FIG. 2 relates $k_A$ and ethylbenzene conversion for several different molecular sieves.

Butane-cracking activity $k_A$ was related to ethylbenzene conversion. Seven non-zeolitic molecular-sieve samples were tested for ethylbenzene conversion at a pressure of 20 atmospheres, temperature of 427° C., and mass hourly space velocity of 4 using a feed of 17 mass % ethylbenzene and 83 mass % meta-xylene. Ethylbenzene ("EB") conversion was chosen as the measure of comparison since ethylbenzene is the most difficult of the C₈-aromatics isomers to convert in an isomerization process. The activity $k_A$ also was determined for the seven samples in accordance with the procedure of Example II. Results were as follows, and also are plotted in FIG. 2:

| Catalyst | EB Conversion, % | $k_A$ |
|---|---|---|
| SAPO-31 | 11 | 0.7 |
| MgAPSO-31 | 34 | 3.8 |
| MnAPSO-31 | 25 | 2.4 |
| MnAPO-31 | 28 | 1.7 |
| CoAPO-31 | 41 | 2.3 |
| CoAPSO-31 | 29 | 2.1 |
| CoAPSO-31 | 44 | 3.7 |

There is a clear correlation between $k_A$ and ethylbenzene conversion, even though there is some scatter in the data points as would be expected from the testing of a variety of molecular sieves.

EXAMPLE IV

The utility of the catalytic composition of the present invention was demonstrated by measuring selectivity to xylenes at varying ethylbenzene conversions. Xylene selectivity is defined as the ratio of potential/actual xylenes in the product.

The catalyst base contained 50 mass % of MgAPSO-31, containing 0.013 mol fraction magnesium, and 50 mass % alumina. The finished catalyst contained, in mass %:

| | |
|---|---|
| platinum | 0.24% |
| chloride | 0.25% |
| sulfur | 0.07% |

Results were compared to those for prior-art catalysts which had been demonstrated to be effective for isomerization of $C_8$ aromatics. One prior-art catalyst was SAPO-11, amounting to 40 mass % of a base along with 40% alumina and 20% silica, in a catalyst containing 0.48 mass % platinum and prepared according to U.S. Pat. No. 4,740,650. Another prior-art catalyst comprised gallium-modified ZSM-5 according to U.S. Pat. No. 4,957,891.

The feedstock used in this example had the following composition in mass %:

| | |
|---|---|
| ethylbenzene | 17% |
| meta-xylene | 58% |
| orthoxylene | 25% |

Figure 3:
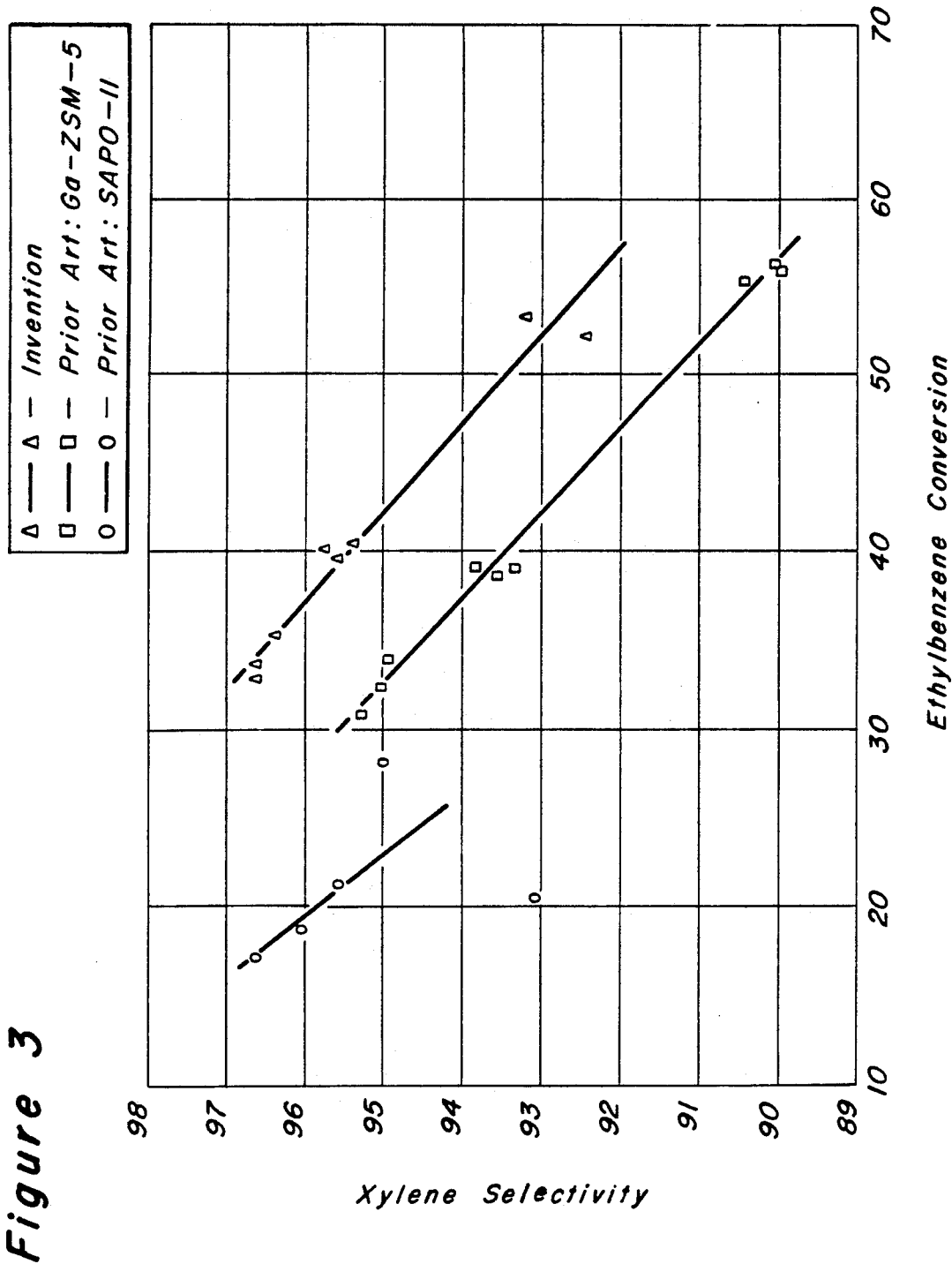
FIG. 3 compares a catalyst of the invention against two catalysts of the prior art with respect to xylene selectivity vs. ethylbenzene conversion.

The results are plotted in FIG. 3 for the catalysts of the invention and of the prior art. The catalyst of the invention shows an advantage of about 2% in xylene selectivity over the gallium-modified-ZSM-5 catalyst and an even greater advantage over the prior-art SAPO-11 catalyst.

EXAMPLE V

Isomerization of an essentially pure ethylbenzene feed was investigated using the catalyst of the invention. The alumina-bound MgAPSO-31 catalyst of Example IV was employed at 427° C. and mass space velocities varying from 6 to 9 as required to achieve a range of ethylbenzene conversions. The proportion of para-xylene in the xylene portion of the product was compared to the thermodynamic equilibrium value at 427° C. Results were as follows:

| Ethylbenzene Conversion % | Para-Xylene % of Equilibrium |
|---|---|
| 21.8 | 173 |
| 24.1 | 168 |
| 29.5 | 155 |

The surprising super-equilibrium yield of para-xylene may indicate, without limiting the invention, that the mechanism of ethylbenzene conversion is selective to para-xylene production.

EXAMPLE VI

Isomerization performance of the catalyst of the invention was investigated when processing a feedstock from which ortho-xylene had been removed. Ortho-xylene, being an industrially important intermediate as noted hereinabove, often is separated from mixed xylene isomers in an aromatics complex by fractionation. In this embodiment of a separation/isomerization process combination, fresh $C_8$-aromatic feed is combined with isomerized product comprising $C_8$-aromatics and naphthenes from the isomerization reaction zone and fed to an fractionator which separates orthoxylene product in a bottoms stream. Overhead from the ortho-xylene fractionator is sent to the para-xylene separation zone; the para-xylene depleted stream is fed to the isomerization reaction zone, where the $C_8$-aromatic isomers are again isomerized to near-equilibrium levels. In this process scheme the $C_8$-aromatic isomers are recycled to extinction, until they are either converted to ortho- or para-xylene or lost due to side-reactions.

Figure 4:
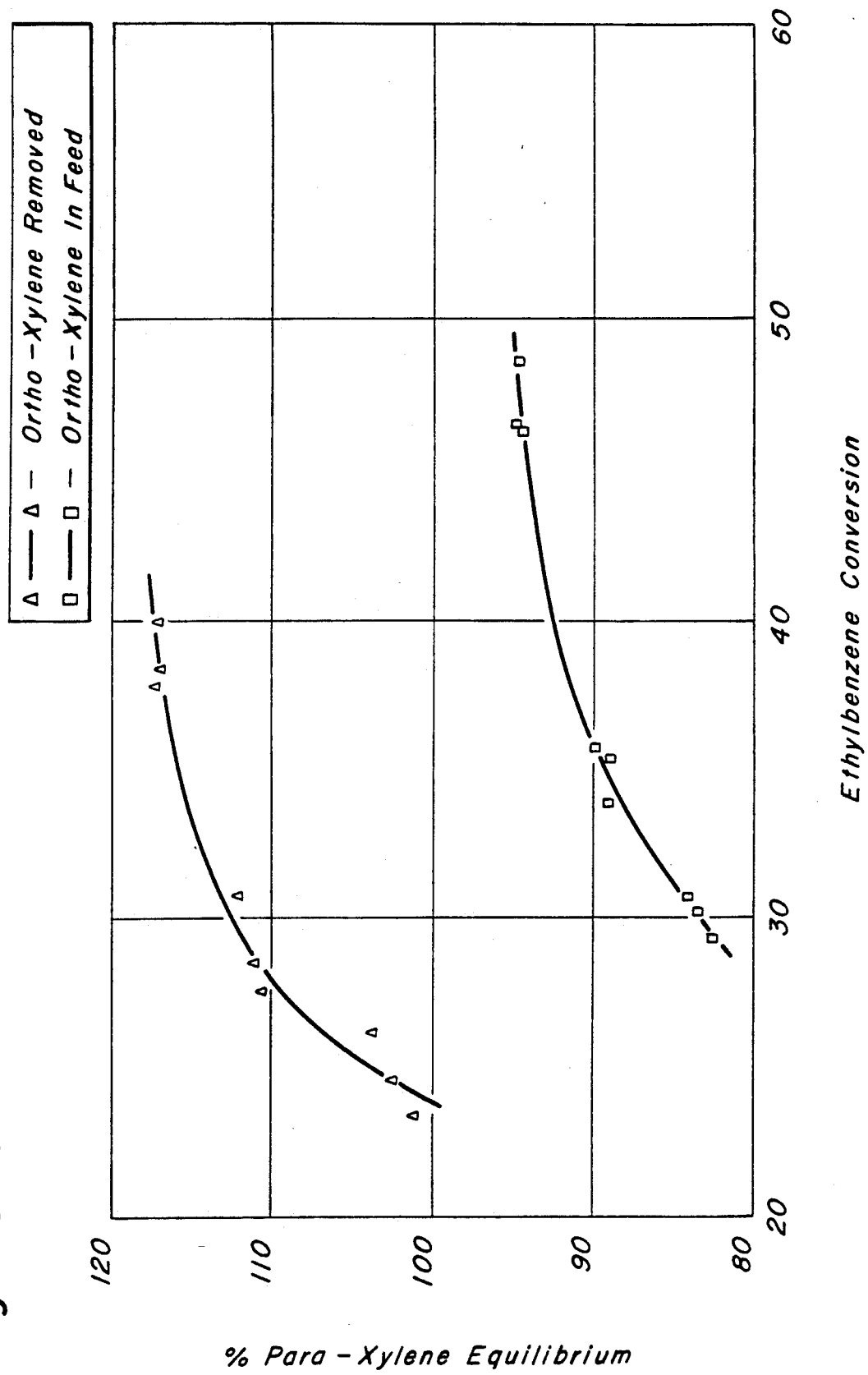
FIG. 4 shows the impact of removing ortho-xylene from the feed on the performance of a catalyst of the invention.

The ortho- and para- depleted feed consisted essentially of 17 mass % ethylbenzene and 83 mass % meta-xylene as described in Example III. Para-xylene content of the xylene portion of the isomerized product was compared to the thermodynamic-equilibrium value at 427° C. in order to determine the % of para-xylene equilibrium and whether a super-equilibrium in excess of 100% had been reached. The results are plotted in FIG. 4: % of para-xylene equilibrium was over 100% for a wide range of ethylbenzene conversions, and approached 120% at 40% ethylbenzene conversion.

We claim:

1. A hydrocarbon-conversion process which comprises contacting a hydrocarbon feedstock, at hydrocarbon-conversion conditions, with a catalytic composition comprising a crystalline MgAPSO molecular sieve which contains from about 0.003 to 0.035 mol fraction of magnesium in the microporous crystalline framework structure to obtain a converted product.

2. The process of claim 1 wherein the content of magnesium in the microporous crystalline framework structure is from about 0.005 to 0.025 mol fraction.

3. The process of claim 1 wherein the MgAPSO comprises MgAPSO-31.

4. The process of claim 1 wherein the non-zeolitic molecular sieve further comprises an $AlPO_4$.

5. The process of claim 1 wherein the catalytic composition further comprises an inorganic-oxide matrix.

6. A process for the isomerization of a non-equilibrium feed mixture of xylenes and ethylbenzene comprising contacting the feed mixture in the presence of hydrogen in an isomerization zone at alkylaromatic-isomerization conditions, with a catalytic composition comprising at least one platinum-group metal component and MgAPSO-31 which contains from about 0.003 to 0.035 mol fraction of magnesium in the microporous crystalline framework structure, to produce an isomerized product.

7. The process of claim 6 wherein the alkylaromatic-isomerization conditions comprise a temperature of from about 300° to 500° C., a pressure of from about 1 to 50 atmospheres, a liquid hourly space velocity of from about 0.5 to 10 $hr^{-1}$ and a hydrogen-to-hydrocarbon mole ratio of from about 0.5:1 to 25:1.

8. The process of claim 6 wherein the content of magnesium in the MgAPSO-31 is from about 0.005 to 0.025 mol fraction in the microporous crystalline framework structure.

9. The process of claim 6 wherein the platinum-group metal component comprises from about 0.1 to 5 mass % platinum on an elemental basis.

10. The process of claim 1 wherein the catalyst further comprises an inorganic-oxide matrix.

11. The process of claim 6 further comprising recovery of para-xylene by selective adsorption from the isomerized product and a fresh $C_8$-aromatic feed.

12. The process of claim 11 wherein ortho-xylene is recovered from one or both of the isomerized product and fresh $C_8$-aromatic feed.

13. The process of claim 12 wherein the isomerized product contains a greater-than-equilibrium concentration of para-xylene.

* * * * *